United States Patent
Yamaguchi et al.

(10) Patent No.: US 7,358,219 B2
(45) Date of Patent: Apr. 15, 2008

(54) FABRIC DEODORIZER COMPRISING AN AMINE OXIDE

(75) Inventors: Noriko Yamaguchi, Wakayama (JP); Ikuo Sugano, Wakayama (JP); Kazutaka Shiratsuchi, Wakayama (JP); Shuji Tagata, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 11/126,262

(22) Filed: May 11, 2005

(65) Prior Publication Data

US 2005/0208013 A1   Sep. 22, 2005

Related U.S. Application Data

(62) Division of application No. 09/913,038, filed as application No. PCT/JP00/01531 on Mar. 14, 2000, now abandoned.

(30) Foreign Application Priority Data

Mar. 16, 1999 (JP) .................. 11-69872

(51) Int. Cl.
*C11D 1/75* (2006.01)
*C11D 3/43* (2006.01)

(52) U.S. Cl. ............. 510/287; 510/276; 510/286; 510/292; 510/293; 510/333; 510/253; 510/373; 510/406; 510/432; 510/477; 510/503; 510/525

(58) Field of Classification Search ........... 510/276, 510/286, 287, 292, 293, 333, 253, 373, 406, 510/432, 477, 503, 525
See application file for complete search history.

(56) References Cited

U.S. PATENT DOCUMENTS

| | | | |
|---|---|---|---|
| 3,617,163 A | 11/1971 | Kalopissis | |
| 3,810,478 A | 5/1974 | Olson et al. | |
| 4,070,309 A | 1/1978 | Jacobsen | |
| 4,180,084 A | 12/1979 | Wegmuller et al. | |
| 4,287,102 A | 9/1981 | Miyajima et al. | |
| 4,391,726 A * | 7/1983 | Koster | 510/299 |
| 4,507,219 A | 3/1985 | Hughes | |
| 4,515,705 A | 5/1985 | Moeddel | |
| 4,548,744 A | 10/1985 | Connor | |
| 4,560,492 A | 12/1985 | Curry et al. | |
| 4,594,184 A | 6/1986 | Cook et al. | |
| 4,791,097 A | 12/1988 | Walele et al. | |
| 4,913,828 A | 4/1990 | Caswell et al. | |
| 5,030,378 A | 7/1991 | Venegas | |
| 5,085,849 A | 2/1992 | Sampson et al. | |
| 5,352,389 A | 10/1994 | Gazzani | |
| 5,578,563 A | 11/1996 | Trinh et al. | |
| 5,759,208 A * | 6/1998 | Zhen et al. | 8/137 |
| 5,816,446 A | 10/1998 | Steindorf et al. | |
| 5,833,970 A | 11/1998 | Cox | |
| 5,981,466 A * | 11/1999 | Morelli et al. | 510/499 |
| 6,046,152 A * | 4/2000 | Vinson et al. | 510/428 |
| 6,110,883 A | 8/2000 | Petri et al. | |
| 6,436,342 B1 * | 8/2002 | Petri et al. | 422/28 |
| 2003/0224960 A1 * | 12/2003 | Scialla et al. | 510/302 |

FOREIGN PATENT DOCUMENTS

| | | |
|---|---|---|
| JP | 61193665 A | 8/1986 |
| JP | 6485367 A | 3/1989 |
| JP | 1207212 A | 8/1989 |
| JP | 4257514 A | 9/1992 |
| JP | 4316676 A | 11/1992 |
| WO | WO-9604940 A | 2/1996 |

* cited by examiner

*Primary Examiner*—Charles Boyer
(74) *Attorney, Agent, or Firm*—Birch, Stewart, Kolasch & Birch, LLP

(57) ABSTRACT

The present invention provides a liquid deodorant having a high deodorizing effect and lasting ability to a fabric or fabrics. That is, the present invention provides a liquid deodorant which comprises 80 to 99% by weight of water and has a pH of 7.5 to 9.5 at 25° C., 1000 ml of which deodorant may be adjusted to pH 10 at 25° C. with 10 to 200 ml of 0.1 N aqueous NaOH and may be adjusted to pH 7 at 25° C. with 20 to 500 ml of 0.1 N aqueous $H_2SO_4$.

6 Claims, No Drawings

FABRIC DEODORIZER COMPRISING AN AMINE OXIDE

This non-provisional application is a divisional of U.S. application Ser. No. 09/913,038, filed on Sep. 19, 2001, now abandoned which is the national phase under 35 U.S.C. § 371 of PCT International Application No. PCT/JP00/01531 which has an International filing date of Mar. 14, 2000, which designated the United States of America, the entire contents of which are hereby incorporated by reference; and this non-provisional application claims priority under 35 U.S.C. § 119(a) on patent application Ser. No. 11-69872 filed in Japan on Mar. 16, 1999, the entire contents of which are also hereby incorporated by reference.

TECHNICAL FIELD

The present invention relates to a deodorant for a fabric or fabrics and relates to a method for deodorizing the same.

BACKGROUND ART

It has become usual that a clothing is laundered every time the clothing is worn, because the custom of laundry have changed. However, a clothing such as a suit and a sweater is hardly laundered in a general home, therefore an amount of laundering the clothing is remarkably less than that of a usual clothing, too. Accordingly, an odor of a body, an odor of a cigarette smoke and an odor of cooking such as grilling meat adhere thereto to cause unpleasant feeling. Further, laundering a carpet, an entrance mat etc. is difficult as well and there is the problem of an unpleasant odor derived from partial dirt thereon.

As disclosed in JP-A 61-193665, JP-A 4-257514 and WO 96/04940 a deodorizing component such as a plant or vegetable extract, a perfume ingredient, cyclodextrin and a metallic salt is incorporated into the deodorant and its composition is conducted to have a buffer capacity. However, there is the problem which provides a deodorizing effect not lasting out although the effect being obtained at first period used.

In addition, an odorous substance as an object of deodorization comprises various substances including an amine-based bad smelling component such as pyridine and an acid-based bad smelling component such as a lower fatty acid. However, the object, which is capable of deodorization by the methods described above, is limited. Thus, there is demand for a deodorant having a high deodorizing effect on various bad smelling components.

Accordingly, the object of the present invention is to provide a liquid deodorant having a high deodorizing performance and lasting ability to a fabric or fabrics.

DISCLOSURE OF INVENTION

The present invention provides a liquid deodorant which comprises 80 to 99% by weight of water and has a pH of 7.5 to 9.5 at 25° C., 1000 ml of which deodorant may be adjusted to pH 10 at 25° C. with 10 to 200 ml of 0.1 N aqueous NaOH and may be adjusted to pH 7 at 25° C. with 20 to 500 ml of 0.1 N aqueous $H_2SO_4$.

The present invention also provides a liquid deodorant which comprises 80 to 99% by weight of water and 0.1 to 2.0% by weight of a compound having at least one group selected from the group consisting of quaternary ammonium groups and amine oxide groups in the molecule and one or two groups selected from $C_8$ to $C_{22}$ alkyl groups and alkenyl groups in the molecule, the deodorant having a pH of 7.5 to 9.5 at 25° C.

Further, the present invention provides a liquid deodorant which comprises 80 to 99% by weight of water and 0.1 to 2.0% by weight of a compound having at least one group selected from the group consisting of quaternary ammonium groups and amine oxide groups in the molecule and one or two groups selected from $C_8$ to $C_{22}$ alkyl groups and alkenyl groups in the molecule, the deodorant having a pH of 7.5 to 9.5 at 25° C., 1000 ml of which deodorant may be adjusted to pH 10 at 25° C. with 10 to 200 ml of 0.1 N aqueous NaOH and may be adjusted to pH 7 at 25° C. with 20 to 500 ml of 0.1 N aqueous $H_2SO_4$.

Furthermore, the present invention provides a method for deodorizing a fabric or fabrics, which comprises spraying the liquid deodorant as defined above onto the fabric as the object of deodorization.

The present invention provides a liquid deodorant device which comprises the liquid deodorant as defined above and a vessel charged with the deodorant, equipped with a manually operated sprayer, too.

The deodorant of the present invention may comprise 88 to 99% by weight of water and the balance including the below explained buffer (a), preferable components such as ethanol and below explained compound (b) and additional water.

The present invention provides use of the liquid as defined above as deodorant.

MODE FOR CARRYING OUT INVENTION

The amount of water in the liquid deodorant of the present invention is 80 to 99% by weight, preferably 90 to 96% by weight, so that the liquid deodorant has satisfactory deodorizing effect while the feeling of a fabric or fabrics is not deteriorated. Further, the pH of the liquid deodorant of the present invention at 25° C. is 7.5 to 9.5, preferably 7.5 to 9.0, so as to obtain satisfactory deodorizing effect on both of an amine-based bad smelling component and a lower fatty acid-based bad smelling components.

The liquid deodorant of the present invention has the property that 10 to 200 ml of 0.1 N aqueous NaOH is necessary for adjustment of 1000 ml of the liquid deodorant having a pH of 7.5 to 9.5 to pH 10 at 25° C. and 20 to 500 ml of 0.1 N aqueous $H_2SO_4$ is necessary for adjustment thereof to pH 7 at 25° C., as mentioned above, (the property is referred to hereinafter as the controlling ability of pH fluctuation).

To obtain such controlling ability of pH fluctuation, it can be achieved by incorporating a combination [referred to hereinafter as Component (a)] of an acid agent, an alkali agent and/or a salt known usually as a buffer solution. Specifically, the acid agent includes a carboxylic acid such as lactic acid, gluconic acid, succinic acid, glutaric acid, adipic acid, malic acid, tartaric acid, maleic acid, fumaric acid, itaconic acid, citric acid, phthalic acid, acetic acid, benzoic acid, salicylic acid and diethyl barbituric acid; an amino acid such as glycine, alanine, valine, leucine, serine, glutamic acid and aspartic acid; and/or an inorganic acid such as phosphoric acid and boric acid. And, specifically, the alkali agent includes an alkanolamine such as triethanolamine as well as an inorganic base such as sodium hydroxide and potassium hydroxide. As the salt may be used a salt formed by neutralization reaction between the above-mentioned acid agent and alkali agent as well as an alkali metal carbonate, an alkali metal silicate and the like.

Among these, an acid agent selected from phosphoric acid, citric acid, succinic acid, maleic acid and fumaric acid and/or an alkali metal salt thereof is preferably incorporated in particular.

Incidentally, as the method for preparing the liquid deodorant in the pH range as the object of the present invention, there can be cited a method which comprises dissolving or dispersing the above-mentioned acid agent, alkali agent and/or salt in water and then adjusting to a given pH range using an acid agent, an alkali agent and/or an aqueous solution thereof. The used acid agent and alkali agent for adjustment may be the same compound as the compound mentioned above. While, an aqueous solution of hydrogen chloride or sulfuric acid may also be used as the acid agent for pH adjustment. Further, an aqueous solution of sodium hydroxide or potassium hydroxide is preferably used as the alkali agent for pH adjustment. The most preferable method for preparing is a method which comprises adding an aqueous solution of sodium hydroxide, hydrogen chloride or sulfuric acid into an aqueous solution the acid agent and/or the salt to adjust a given pH.

Component (a) is incorporated in such an amount as to have a given controlling ability of pH fluctuation. Incidentally, the content of an acid agent selected from phosphoric acid, citric acid, succinic acid, maleic acid and fumaric acid and/or an alkali metal salt thereof as the above-mentioned preferable compound in the liquid deodorant is preferably 0.01 to 3.0% by weight, more preferably 0.05 to 2.0% by weight.

In the present invention, it is preferable that a compound having at least one group selected from quaternary ammonium groups and amine oxide groups and having one or two groups, preferably one group, selected from $C_8$ to $C_{22}$ alkyl groups and alkenyl groups in the molecule is further incorporated as Component (b). Such a compound exhibits deodorizing effect due to the controlling ability of pH fluctuation and further acts for controlling vaporization of odorous components. Therefore, higher deodorizing effect can be maintained while the lasting ability of deodorization after treatment tends to be improved.

Component (b) may include a quaternary ammonium salt-based surfactant and an amphoteric surfactant such as a sulfobetaine, a carbobetaine and an amine oxide. When it is used as a deodorant for a fabric or fabrics, using a quaternary ammonium salt- or amine oxide-based surfactant having one group selected from $C_8$ to $C_{18}$ alkyl groups and alkenyl groups, among these, is preferable, using the quaternary ammonium salt of the following formula (I) and the amine oxide of the following formula (II) or (III) is more preferable, and using the amine oxide of the following formula (III) is most preferable:

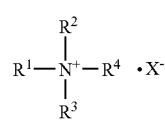

(I)

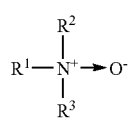

(II)

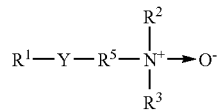

(III)

wherein $R^1$ is a $C_8$ to $C_{18}$ alkyl group or alkenyl group; each of $R^2$, $R^3$ and $R^4$ is a $C_1$ to $C_3$ alkyl group or hydroxyalkyl group; $R^5$ is a $C_1$ to $C_5$ alkylene group; Y is —$CONR^6$—, —$NR^6CO$—, —COO— or —OCO— whereupon $R^6$ is a hydrogen atom or a $C_1$ to $C_3$ alkyl group; X is a halogen ion, a $C_1$ to $C_{14}$ fatty acid or a $C_1$ to $C_3$ alkyl sulfate.

Component (b) may be comprised in an amount of 0.1 to 2.0% by weight, preferably 0.2 to 1.5% by weight, in the liquid deodorant so that satisfactorily lasting ability of deodorization and the feeling of fabrics are not deteriorated.

In the present invention, a high deodorizing effect and lasting ability can be obtained by using either Component (a) or (b), but simultaneous use of Components (a) and (b) is particularly preferable.

For easily drying by facilitating vaporization of the liquid deodorant from a fabric or fabrics after treatment, ethanol is comprised in an amount of preferably 1 to 10% by weight, more preferably 2 to 8% by weight, too. Incidentally, a denatured ethanol may be used as this ethanol, and in particular 8-acetylated sucrose-denatured ethanol or sodium polyoxyethylene alkyl ether sulfate-denatured ethanol is preferably used.

A perfume component is used in consideration of masking action to become more preferable finishing. As the perfume component, a compound not affected by the other components is selected.

The liquid deodorant of the present invention further can be incorporated with lower ($C_3$ to $C_4$) alcohols such as isopropanol, polyhydric ($C_2$ to $C_{12}$) alcohols such as ethylene glycol, propylene glycol, glycerol and sorbitol, and aromatic sulfonates such as p-toluene sulfonate and m-xylene sulfonate, as solubilizer. Further, a dye, a thickener and the like may be incorporated if necessary, and a preservative•fungicide is preferably incorporated when antibacterial ability is worried because of no or little ethanol being incorporated.

As the liquid deodorant of the present invention, one which does not foam at spraying itself is preferable. For spraying it as uniform droplet-particles with less foaming, the content of the surfactant other than Component (b) is not more than 2.0% by weight, preferably not more than 1.5% by weight, particularly preferably not more than 1.0% by weight.

The method for using the liquid deodorant of the present invention is preferably a method for using the liquid deodorant which comprises spraying it onto a fabric. In particular, a method for spraying by a sprayer is preferable. The sprayer is preferably a trigger-type spray. In particular, it is good to use a pressure-keeping-type trigger which is excellent in uniformity of liquid-dripping and of spraying and which looks like one shown in FIG. 1 of JP-U 4-37554.

The used amount of liquid deodorant is such an amount that a fabric is moistened therewith, in the case that the liquid deodorant is rubbed on the fabric. While, in the case of spraying the liquid deodorant onto a fabric, the ratio of 0.2 to 0.7 g of the liquid deodorant to 100 to 800 cm² of the fabric is preferable.

INDUSTRIAL APPLICABILITY

The liquid deodorant of the present invention exhibits a high deodorizing performance from first period used when the liquid deodorant is used for a fabric, a non-woven fabric, a woven fabric, a clothing, a product made of fiber, a fibrous product and other fiber products. And then, the liquid deodorant is also excellent in lasting ability of its high deodorizing effect.

EXAMPLES

Incorporation Examples 1 to 8

Liquid deodorants having the compositions shown in Table 1 were prepared. Incidentally, the liquid deodorants were adjusted to pH 8.5 with 0.1 N NaOH. The objects of deodorization described below were used and treated by the following method for deodorizing. Immediately after the treatment, the deodorizing performance was examined. And, while, after drying for 24 hours without exposure to sunlight in a room (20° C.), the deodorizing performance was examined. These results are shown in Table 1.

<Preparation of the Objects of Deodorization>

Preparation of a Fabric Adhered with an Odor of a Cigarette Smoke

On one wall of a closed smoking room having the floor area of 5×5 m and the height of 3 m, 1×1 m of cotton shirting cloth 2003# was suspended perpendicularly to the floor such that the height from the floor to the upper end of the cloth was 3 m. In this smoking room, each and all of 10 men smoked 3 cigarettes for 2 hours. Thereafter, the above-mentioned cloth was cut into the size of 20×20 cm as test pieces and the pieces were subjected to the experiment.

Preparation of a Fabric Adhered with an Odor of Sweat

Underclothes (an undershirt with half-length sleeves, the tradename of Gunze YG, manufactured by Gunze Ltd.) worn for 24 hours by 10 men were charged into a vinyl plastic bag. The vinyl plastic bag was enclosed, and then was left for 3 days in a room. Thereafter, the underclothes were cut into the size of 20×20 cm as test pieces and subjected to the experiment.

<Method for Deodorizing>

Four hundreds ml of liquid deodorant was charged into a vessel of a commercially manually operated sprayer (that is, 400 ml of the content is removed from a vessel of Smoother for an electric iron, manufactured by Kao Corp., the vessel for a manually operated sprayer was washed until its odor disappeared, and the vessel was air-dried). This liquid deodorant was sprayed twice so as to be spread over the whole of the objects of deodorization.

<Evaluation of Deodorizing Performance>

Ten panelists including thirties-year-old men and women (being 5 men and 5 women) smelled the objects of deodorization. Then, they evaluated in the following method for indicating odor strength by 6-rank. The average point thereof was determined. The average point was shown by ⊚ as from not less than 0 to less than 1, by ○ as from not less than 1 to less than 2, by Δ as from not less than 2 to less than 3, and by X as not less than 3 to not more than 5. ⊚ or ○ is preferable.

0: Odorless.
1: The strength of unidentified but faintly felt odor (level of threshold value so as to be detected).
2: The strength of identified and easily felt and weak odor (level of threshold value so as to be recognized).
3: Apparently felt odor.
4: Strong odor.
5: Too strong odor to endure.

TABLE 1

| | Incorporated components | Incorporation Examples | | | | | | | |
|---|---|---|---|---|---|---|---|---|---|
| | (% by weight) | 1 | 2 | 3 | 4 | 5 | 6 | 7 | 8 |
| (a) | sodium dihydrogen phosphate | 0.2 | | 0.2 | | 0.2 | | | |
| | citric acid | | 0.5 | | | | | 0.5 | 0.5 |
| (b) | Amidopropylamine oxide[1] | 1 | | | | | | | |
| | Q-40ES[2] | | 1 | | | | | | |
| | Lauryldimethylamine oxide | | | 1 | 1 | | | | |
| | Ethanol[3] | 5 | 5 | 5 | 5 | 5 | 5 | 5 | 5 |
| | Deionized water and 0.1 N NaOH | Balance | Balance | Balance | Balance | Balance | Balance | Balance | Balance |
| | Total amount (% by weight) | 100 | 100 | 100 | 100 | 100 | 100 | 100 | 100 |
| | pH at 25° C. | 8.5 | 8.5 | 8.5 | 8.5 | 8.5 | 8.5 | 10 | 7 |
| | Necessary amount of 0.1 N NaOH (ml) | 25 | 15 | 25 | 5 | 22 | 5 | 0 | 250 |
| | Necessary amount of 0.1 N $H_2SO_4$ (ml) | 145 | 25 | 140 | 12 | 136 | 12 | 180 | 0 |
| Odor of cigarette smoke | Deodorizing performance immediately after treatment | ⊚ | ⊚ | ⊚ | ○ | ○ | Δ | Δ | Δ |
| | Deodorizing performance after 24 hours | ○ | ○ | ○ | ○ | Δ | X | X | Δ |
| Odor of sweat | Deodorizing performance immediately after treatment | ⊚ | ⊚ | ⊚ | ○ | ○ | Δ | Δ | Δ |
| | Deodorizing performance after 24 hours | ○ | ○ | ○ | ○ | Δ | Δ | Δ | X |

[1] A compound obtained by reacting an amidated product of lauric acid and dimethylaminopropyl amine with hydrogen peroxide (that is, the compound of the formula (III) wherein $R^1$ is an alkyl group having 12 carbon atoms, $R^2$ and $R^3$ are methyl groups, $R^5$ is a propylene group, Y is —$CONR^6$— and $R^6$ is a hydrogen atom).
[2] N-tetradecyl-N,N-dimethyl-N-ethyl quaternary ammonium ethyl sulfate.
[3] 8-acetylated sucrose-denatured ethanol.

The invention claimed is:

1. A deodorizing method, which comprises the step of spraying onto a fabric, which is the object of deodorization, a liquid deodorant, which comprises:
   80 to 99% by weight of water,
   0.1 to 2.0% by weight of a compound having at least one amine oxide group in the molecule and one or two groups selected from $C_8$ to $C_{22}$ alkyl groups and alkenyl groups in the molecule, and
   a buffer solution comprising the combination of (i) an acid agent which is succinic acid, maleic acid, fumaric acid, citric acid, phosphoric acid or an alkali metal salt thereof, and (ii) an alkali agent and/or a salt thereof in such an amount that the deodorant has a pH value of 7.5 to 9.5 at 25° C., and 1000 ml of the deodorant may be adjusted to pH 10 at 25° C. with 10 to 200 ml of 0.1 N aqueous NaOH and maybe adjusted to pH 7 at 25° C. with 20 to 500 ml of 0.1 N aqueous $H_2SO_4$;
   wherein the content of a surfactant in the liquid deodorant, other than said compound having at least one amine oxide group in the molecule and one or two groups selected from $C_8$ to $C_{22}$ alkyl groups and alkenyl groups in the molecule, is not more than 2.0% by weight,
   wherein the content of the acid agent or the alkali metal salt thereof in the liquid deodorant is 0.01 to 3.0% by weight, and
   wherein the liquid deodorant additionally comprises 1-10% by weight of ethanol.

2. The deodorizing method according to claim 1, which comprises the step of spraying the liquid deodorant onto said fabric, which is the object of deodorization, with a sprayer.

3. The deodorizing method according to claim 1, which comprises the step of spraying the liquid deodorant onto said fabric, which is the object of deodorization, with a trigger-type sprayer.

4. The deodorizing method according to claim 1, wherein the content of said acid agent or the alkali metal salt thereof in the liquid deodorant is from 0.05 to 2.0% by weight.

5. The deodorizing method according to claim 1, wherein the liquid deodorant comprises 2-8% by weight of ethanol.

6. The deodorizing method according to claim 1, wherein the compound having at least one amine oxide group and one or two groups selected from $C_8$ to $C_{22}$ alkyl groups and alkenyl groups in the molecule is represented by a compound of one of the following formulas (II) and (III):

(II)

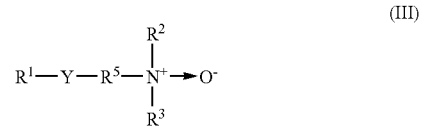

(III)

wherein $R^1$ is a $C_8$ to $C_{18}$ alkyl group or alkenyl group; each of $R^2$ and $R^3$ is a $C_1$ to $C_3$ alkyl group or hydroxyalkyl group; $R^5$ is a $C_1$ to $C_5$ alkylene group;

Y is —$CONR^6$—, —$NR^6CO$—, —COO— or whereupon $R^6$ a hydrogen atom or a $C_1$ to $C_3$ alkyl group.

* * * * *